United States Patent

Ricca et al.

[11] Patent Number: 5,817,885
[45] Date of Patent: *Oct. 6, 1998

[54] DERIVATIVES OF TERPENE ORIGIN, SURFACTANT AND/OR FRAGRANT COMPOSITION CONTAINING THEM AND DETERGENT FORMULATION BASED ON THIS COMPOSITION

[75] Inventors: Jean-Marc Ricca, Lyons; Paul-Noël Derian, Fontenay Aux Roses; Jean-Pierre Hecaen, Stains; Jean-Michel Mercier, Thiais, all of France

[73] Assignee: Rhone-Poulenc Chimie, Courbevoie Cedex, France

[ * ] Notice: The term of this patent shall not extend beyond the expiration date of Pat. No. 5,674,823.

[21] Appl. No.: 877,908

[22] Filed: Jun. 18, 1997

Related U.S. Application Data

[62] Division of Ser. No. 498,261, Jul. 3, 1995, Pat. No. 5,674,823.

[30] Foreign Application Priority Data

Jul. 1, 1994 [FR] France ................... 94 08 366

[51] Int. Cl.$^6$ ................ C11D 3/16; C11D 3/37; A61K 7/46; C07C 43/18
[52] U.S. Cl. .............. 568/612; 510/102; 510/107; 510/535; 512/8; 512/25; 528/393
[58] Field of Search ................. 510/102, 107, 510/506, 535, 496; 512/8, 25; 528/393; 568/612

[56] References Cited

U.S. PATENT DOCUMENTS

| | | | |
|---|---|---|---|
| 3,354,225 | 11/1967 | Kane | 260/611 |
| 3,359,327 | 12/1967 | Roberts et al. | 568/612 |
| 3,370,080 | 2/1968 | Bloch | 260/457 |
| 3,798,253 | 3/1974 | Rick et al. | 260/448.2 B |
| 4,620,028 | 10/1986 | Gorman et al. | 560/193 |
| 4,756,840 | 7/1988 | Sprecker et al. | 510/102 |

FOREIGN PATENT DOCUMENTS

| | | |
|---|---|---|
| 1294933 | 10/1962 | France . |
| 2429213 | 1/1980 | France . |
| 3822202 | 1/1990 | Germany . |
| 61-233650 | 10/1986 | Japan . |

OTHER PUBLICATIONS

N. Imamura et al, "Unsaturated Esters of Nopol or Derivatives," *Chemical Abstracts*, vol. 106, No. 22, Jun. 1, 1987.

Primary Examiner—Mark Kopec
Attorney, Agent, or Firm—Burns, Doane, Swecker & Mathis, L.L.P.

[57] ABSTRACT

The present invention relates to novel derivatives of terpene origin which consist of cycloalkenyls or cycloalkyls having at least seven carbon atoms and possessing surfactant and/or fragrant properties. According to one embodiment, the invention relates to compounds of the formula $$\text{(terpene)}-(CH_2-CH_2)_{m=0\,or\,1}-O-(CH_2-CH-O)_p\text{-}(CH_2-CH_2-O)_q-H$$
with side chain $CH_3$ in which p and q are integers or decimal numbers and are not equal to zero, $0 \leq p \leq 20$, preferably, $0 \leq p \leq 5$, and $0 \leq q \leq 100$, preferably $1 \leq q \leq 20$. The invention further relates to the surfactant and/or fragrant compositions based on the above-mentioned compounds. The invention has particular applicability in detergent and perfume formulations.

23 Claims, 1 Drawing Sheet

DERIVATIVES OF TERPENE ORIGIN, SURFACTANT AND/OR FRAGRANT COMPOSITION CONTAINING THEM AND DETERGENT FORMULATION BASED ON THIS COMPOSITION

This application is a divisional of application Ser. No. 08/498,261, filed Jul. 3, 1995, now U.S. Pat. No. 5,674,823.

BACKGROUND OF THE INVENTION

1. Field of the Invention

The present invention relates to novel derivatives of terpene origin which consist of cycloalkenyls or cycloalkyls having at least seven carbon atoms and possessing surfactant and/or fragrant properties.

Apart from this novel chemical product feature, the field of application of the present invention is that of surfactant and/or fragrant compounds.

2. Description of the Prior Art

The compounds according to the invention belong to an extensive family of chemicals comprising especially and most importantly the derivatives of NOPOL or 6,6-dimethylbicyclo[3.1.1]hept-2-en-2-ethanol. NOPOL is a terpene obtained by reacting pinene with formaldehyde. It is used in the form of NOPOL acetate in the field of perfumery. However, there has never been any reference to any kind of application of this type of compound in the surfactants sector.

Japanese patent no. 61-233 650 discloses saturated NOPOL esters and derivatives thereof. These esters have the following formula:

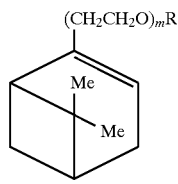

in which R is an acrylate radical and m=1 or 2.

These acrylic acid esters are intended for use as monomers in the manufacture of poly(meth)acrylates, which in turn are intended for use as starting materials in the manufacture of optical lenses. Very specific NOPOL derivatives are therefore involved here. Although these derivatives admittedly belong to the cycloalkenyl family, they constitute a subgroup specifically limited to the restricted field of the poly-(meth)acrylates.

German patent application no. 38 22 202 also discloses NOPOL acrylate esters of the following formula:

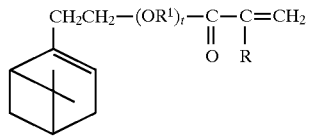

in which $R^1 = C_2-C_4$-alkyl, R=H or $CH_3$ and t is between 0 and 10. These NOPOL acrylate esters constitute repeat units of acrylate homopolymers or copolymers useful as concrete additives (hardeners). Here again the chemical structure is of the polyalkylen-alkoxylated NOPOL acrylate ester type. These products also belong to the restricted and well-defined subgroup of the poly(meth)acrylates.

Like the lens manufacturing application referred to above, the concrete hardening application has nothing to do with the surfactant and/or fragrant functions which are of interest within the framework of the invention.

In another field which is poles apart from that of surfactants, French patent application no. 2 429 213 incidentally discloses a precursor of norpinane derivatives useful as antispasmodics, which are the subject of said patent application. This precursor is an isolated product of the formula 2-[2-(6,6-dimethylnor-pinan-2-yl)ethoxy]ethanol. Said patent application makes no reference to the specific properties of this synthesis intermediate.

The family of chemicals on which the invention is based also includes derivatives of arbanol, a terpene compound derived from camphane and having the following formula:

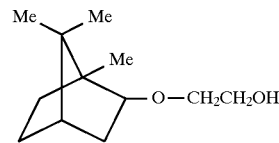

U.S. Pat. Nos. 3,354,225 and 4,620,028 describe the ethoxyhydroxylated camphane derivative (arbanol) or propoxyhydroxylated camphane derivative. According to U.S. Pat. No. 4,620,028, the oxyalkylene graft can contain 2 to 4 ethoxy or propoxy units.

Said U.S. patents make no mention of specific properties for these camphane derivatives, apart from their fragrant property.

The prior art of the invention also relates to the field of detergency. Thus, among the known surfactants, those most widely used on the industrial scale, for example in detergency, are especially the poly-alkoxylated linear fatty alcohols such as, for example, polyethoxylated dodecanol or lauryl alcohol. For lack of a better reason, these surfactants are only indispensable because of the low cost of their synthesis. The assets of these products are not in fact in their surfactant power since this is relatively low and hence not entirely satisfactory.

By contrast, the (poly)alkoxylated alkyl-phenols, which are also industrial surfactants, possess relatively good surfactant properties but remain of limited use on account of their toxicity and their harmful effects on the environment.

Furthermore, these known surfactants all share a major disadvantage, namely their tendency to produce foam. This is particularly troublesome in both industrial and domestic detergency.

BRIEF SUMMARY OF THE INVENTION

In the present state of knowledge, one of the essential objects of the present invention is to provide novel chemicals which, in particular, behave well as surfactants.

A further object of the invention is to provide novel surfactant chemicals which are easy and economic to obtain.

A further object of the invention is to provide novel surfactant compounds which have the lowest possible toxicity and, by the same token, benefit from the advantageous characteristic of not polluting the environment.

A further object of the invention is to provide novel surfactant chemicals which have a pleasant odor and do not foam.

A further object of the invention is to provide a simple and inexpensive process for the preparation of novel chemicals, especially surfactant chemicals, of the type referred to above.

It is in this context that the Applicant has conducted lengthy and laborious researches and experiments which, to its credit, have ultimately enabled it, totally surprisingly and unexpectedly, to isolate a novel class of chemical products which possess very good surfactant properties, in particular, and which belong to the chemical family of the polyalkoxylated cycloalkenyl(oxy)alkylenes or cycloalkyl(oxy) alkylenes.

Thus the present invention achieves the above-mentioned objects, inter alia, by proposing compounds of the following formula:

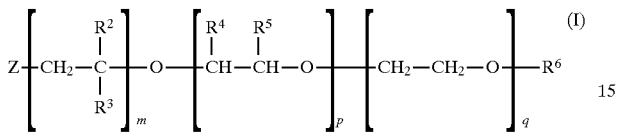

in which:

* Z is a bicyclo[a.b.c]heptenyl or bicyclo[a.b.c]heptyl radical, where:
  ⊕ a+b+c=5,
  ⊕ a=2, 3 or 4,
  ⊕ b=2 or 1,
  ⊕ c=0 or 1, said radical optionally being substituted by at least one $C_1$–$C_6$-alkyl, preferably a methyl, and comprising a skeleton selected from those mentioned below ($Z_1$ to $Z_7$) and from their heptyl analogs without the double bond:

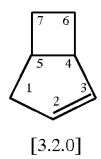
[3.2.0]

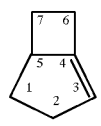
[3.2.0]

[2.2.1]

[3.1.1]

[3.1.1]

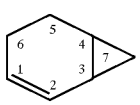
[4.1.0]

-continued

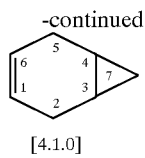
[4.1.0]

$R^2$ and $R^3$ are identical or different and are hydrogen or a linear or branched (cyclo)alkyl or (cyclo)alkenyl group, preferably a linear or branched $C_1$–$C_{22}$-(cyclo)alkyl group, hydrogen and methyl being more particularly preferred;

$R^4$ and $R^5$ are identical or different and are hydrogen or a linear or branched (cyclo)alkyl or (cyclo)alkenyl radical, preferably a linear or branched $C_1$–$C_{22}$-(cyclo)alkyl radical, hydrogen, methyl and ethyl being more particularly preferred;

$R^6$ is hydrogen or one of the following groups: $SO_3M$, $OPO_3(M)_2$, —$(CH_2)_m$—COOM, where m is between 1 and 6, or —$(CH_2)_z$—$SO_3M$, where z=1 to 6, in which groups M=H, Na, K, Li or $N(R^7)_4^+$, where $R^7$=H or a $C_1$–$C_{22}$-(cyclo)alkyl, preferably a $C_1$–$C_6$-(cyclo)alkyl, which may be hydroxylated, hydrogen, methyl and hydroxyethyl being preferred;

m=0 or 1, $1 \leq p \leq 20$, preferably $1 \leq p \leq 10$ and particularly preferably $1 \leq p \leq 3$, and $1 \leq q \leq 200$, preferably $1 \leq q \leq 50$ and particularly preferably $1 \leq q \leq 10$, with the proviso that when m=0, at least one of the substituents $R^4$ and $R^5$ is other than hydrogen.

DETAILED DESCRIPTION OF THE PREFERRED EMBODIMENTS OF THE INVENTION

Figure 1:
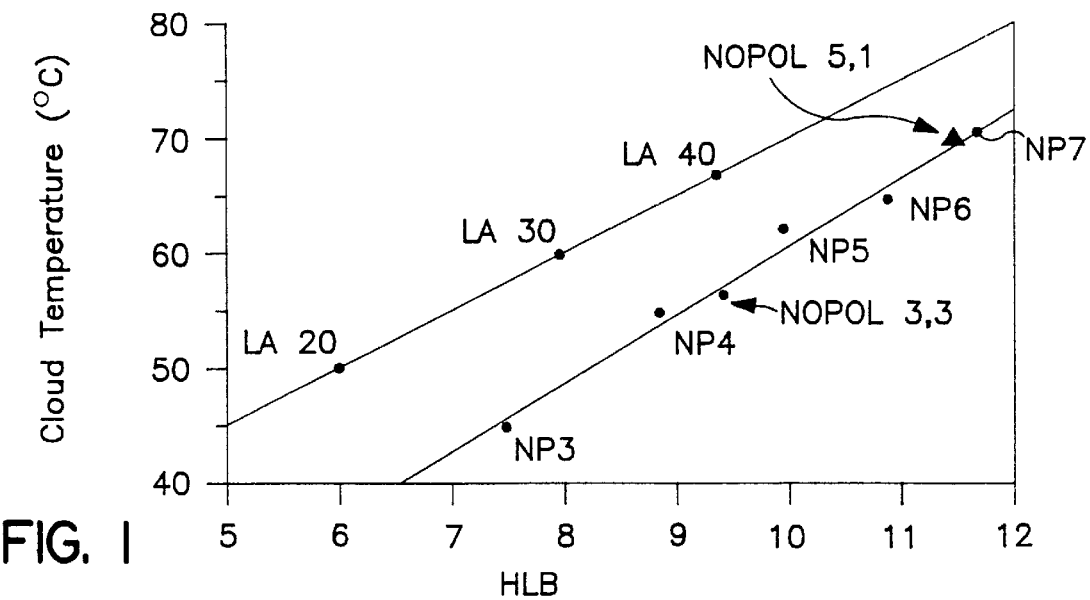

The compounds of terpene origin according to the invention form a particular class of chemicals which constitutes a novel selection from within the family of the polyalkoxylated cycloalkenyl(oxy)alkylenes or cycloalkyl(oxy) alkylenes. In particular, the compounds of this class have surfactant and non-foaming and/or fragrant properties of very considerable value.

In formula (I), the radical Z is preferably attached to the rest of the chain via any one of its carbons $C_1$ to $C_6$, carbons $C_1$, $C_5$ and $C_6$ being more preferably selected.

In the case of bicycloheptanes or bicyclo-heptenes joined to a polyalkoxylated chain via an oxygen bridge (m=0), provision is made for either $R^4$ or $R^5$ not to be hydrogen.

A possible example, therefore, is to have $R^4$=H and $R^5$=$C_1$–$C_6$-alkyl, preferably methyl.

Furthermore, it must be considered that the position of the repeat units identified by the parameters p and q in the graft of Z (formula I) is not limiting. The sequence shown in formula (I) is only one of many examples.

According to a preferred modality of the invention, the radical Z of the compounds (I) is substituted on at least one of its carbons by at least two $C_1$–$C_6$-alkyl groups, preferably by two $CH_3$ groups advantageously located on carbon 7 of Z.

A first subfamily of compounds, (Ia), which is used more particularly, is the one consisting of the compounds (I) in which m=1 and the radical Z is selected from the list comprising the above-defined radicals $Z_3$ to $Z_7$ substituted on carbon 7 by two methyls.

The skeletons $Z_4$ and $Z_5$ substituted on $C_7$ by two $CH_3$ groups are preferred skeletons Z in the sub-family (Ia).

The more particularly preferred compounds (Ia) according to the invention are terpene derivatives in which m=1 in formula (I), particularly pinene derivatives and even more particularly NOPOL derivatives.

A second valuable subfamily of compounds according to the invention, (Ib), is the one consisting of the compounds (I) in which m=0 and the radical Z comprises the heptyl analog, without the double bond, of the skeleton $Z_3$.

In this subfamily (Ib), the heptyl analog of $Z_3$ advantageously comprises two methyls on carbon 7, this analog preferably being substituted by at least one alkyl radical—advantageously a $C_1$-$C_6$-alkyl radical—and preferably by at least one methyl, on carbon 2 or 5. The case of a methyl substituent on carbon 5 corresponds to a bornyl or isobornyl radical, according to the spatial location of the $CH_3$ on $C_5$.

Now, the preferred compounds (Ib) are precisely those in which m=0 and Z=$Z_3$ of the (iso)bornyl type:

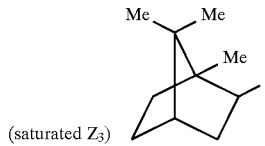

(saturated $Z_3$)

Advantageously, the repeat units of formula (I) identified by the parameters p and q are present in such an amount and arranged in such a way as to form a random or block polymer chain, preferably a block polymer chain with the order given in formula (I).

Thus, within the framework of the invention, the interest is more specifically, but without implying a limitation, in products resulting from the ethoxylation and/or propoxylation of NOPOL (Ia) and ARBANOL (Ib). These reactions lead to the formation of a polyethylene oxide and/or polypropylene oxide chain, which constitutes the hydrophilic pole of the surfactant molecule.

The surfactant properties of these compounds are quite considerable. These properties can be evaluated e.g. by means of known analytical techniques based on measurement of the cloud point as a function of the hydrophilic lipophilic balance (HLB).

Thus it has been possible to observe that the surfactant behavior of the compounds according to the invention is better than or substantially equivalent to that of the known (but toxic) surfactants, namely the ethoxylated nonylphenols. Moreover, the surfactant performance characteristics of the compounds of the invention remain acceptable compared with those of the linear fatty alcohols such as the lauryl alcohols.

However, the particularly advantageous properties of the compounds according to the invention, which have to be stressed, are their non-foaming effect and the absence of an unpleasant odor.

Furthermore, it should be emphasized that the compounds (I), some of which are of natural origin, have a relatively low toxicity and no harmful effects on the environment.

These compounds (I) are also valuable in that they can be obtained relatively easily at an acceptable cost.

Thus the compounds (Ia) [m=1], with the dual function of surfactant and perfume, can be prepared by carrying out a process which consists essentially in reacting a reactant of formula (I'):

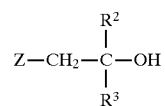

with a reactant (Wop) of the formula

and then, preferably,
with a reactant (Woe) of the formula

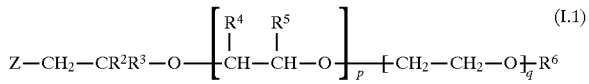

in which formulae:
Z is as defined in claims 1, 2, 3 or 4,
$R^2$ and $R^3$ are identical or different and are hydrogen or a linear or branched $C_1$-$C_{22}$-(cyclo)alkyl or -(cyclo)alkenyl, hydrogen and methyl being more particularly preferred, and
$R^4$ and $R^5$ are identical or different and are hydrogen or a linear or branched (cyclo)alkyl or (cyclo)alkenyl radical, preferably a linear or branched $C_1$-$C_{22}$-(cyclo)alkyl radical, hydrogen, methyl and ethyl being more particularly preferred, with the proviso that at least one of the substituents $R^4$ and $R^5$ is other than hydrogen,
to give a product (I.1):

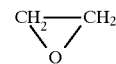

where p, q and $R^6$ are as defined above.

This reaction is carried out in the presence of an effective amount of a catalyst and at a temperature above 100° C., preferably of between 120° and 250° C. and particularly preferably of between 150° C. and 200° C.

As regards the compounds (Ib), in which m=0, they can be prepared by the process which consists essentially in reacting a reactant of formula (I"):

in which the definitions of $R^4$ and $R^5$ correspond to those given above, with a reactant (Wop), of the formula defined above, and then, preferably, with a reactant (Woe), also of the formula defined above, to give a product (I.2):

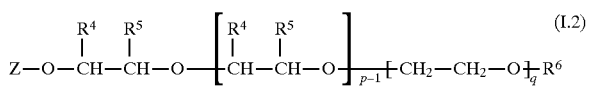

where p, q and $R^6$ are as defined above.

This reaction is carried out in the presence of an effective amount of a catalyst and at a temperature above 100° C., preferably of between 120° and 250° C. and particularly preferably of between 150° C. and 200° C.

The reactions (I') or (I")+(Wop and Woe) are optionally followed by a functionalization, the purpose of which is to convert the terminal hydrogen to one of the other substituents $R^6$ as defined above.

The compounds of general formula (I') can be obtained by a condensation reaction between on the one hand bicyclic alkylene precursors carrying an exocyclic double bond, the structures of which are similar to those of the radicals Z defined above, and on the other hand compounds carrying a carbonyl group of the aldehyde or ketone type.

These bicyclic compounds are advantageously bicyclo [a.b.c]-n-alkyleneheptanes, preferably bicyclo-[a.b.c]-n-methyleneheptanes, where n=1 to 6 and a+b+c=5.

Examples of such compounds which may be mentioned are bicyclo[3.2.0]-2-methyleneheptane, bicyclo-[2.2.1]-2-methyleneheptane, 2-methylenenorbornane, 1-methyl-2-methylenenorbornane, isosantene and β-pinene, this last product being particularly preferred.

Among the compounds with a carbonyl group, it is preferable to use aldehydes and even more preferable to use saturated linear aldehydes, formaldehyde being particularly preferred.

Formaldehyde can be used in its various forms: aqueous solution, trioxane or paraformaldehyde. If appropriate, formaldehyde can be employed in the gaseous form by depolymerizing paraformaldehyde under the action of heat.

The condensation reaction can be carried out in the liquid or gas phase under atmospheric or autogenous pressure.

According to an original characteristic of the invention, the process for the preparation of the products (I') therefore consists essentially of a condensation reaction between at least one bicyclo-[a.b.c]-n-alkyleneheptane (where n=1 to 6 and a+b+c=5) and at least one carbonyl compound, said condensation reaction advantageously being carried out in the absence of a solvent and, if appropriate, in the presence of a catalyst.

The use of an inert solvent can also be envisaged. Among the compatible solvents, there may be mentioned organochlorinated solvents such as dichloro-methane, chloroform and carbon tetrachloride, aromatic solvents such as benzene, toluene and xylenes, chloro-aromatics such as chloro- and dichloro-benzenes, alcohol solvents such as linear or branched alcohols ($C_1$–$C_{22}$) and cyclic alcohols like cyclohexanol, and solvents of the alkene type such as alpha-pinene or camphene.

In practice, it is thus possible to make provision for the reaction to take place for example in the presence of alpha-pinene in a ratio of 0.5–10 mol of alpha-pinene per mol of precursor.

The products (I') are generally obtained in the form of a liquid or solid, after distillation of the solvent where appropriate, and purified by distillation or crystallization.

This reaction can advantageously be improved by the use of homogeneous or heterogeneous catalysts based on homogeneous or supported Lewis acids. Among the Lewis acids, there may be mentioned aluminum and titanium alkoxides and halogenated derivatives of aluminum, titanium, iron, zinc and boron.

Iron and zinc derivatives, such as iron trichloride and zinc dichloride, especially zinc dichloride, are particularly preferred.

These catalysts are employed in a ratio of 0.001 to 0.5 mol of catalyst per mol of precursor, preferably of 0.01 to 0.1 mol/mol.

After the reaction, the catalysts are removed by filtration or by washing with alkaline solutions.

The condensation reaction is carried out in a temperature range of 50°–300° C. in the liquid phase under autogenous pressure, or of 250°–600° C. in the gas phase. It is preferably carried out in the liquid phase at 120°–240° C., preferably 150°–200° C.

The carbonyl compound is used in ratios of 0.5–10 mol per mol of precursor of (I'), preferably of 0.5–2.

Any excess can be separated off after the reaction by filtration or distillation.

It should be emphasized that the compound (I') corresponding to the compounds having a radical $Z_4$ and $Z_5$, respectively, is NOPOL.

As regards the reactants (Woe and Wop), it is preferable to use ethylene oxide, propylene oxide, butylene oxide or mixtures thereof, ethylene oxide, propylene oxide or mixtures thereof being preferred.

The amount of reactants to be brought into contact can vary within wide limits.

The alkylene oxide is generally in excess relative to the bicyclic aliphatic alcohol (I'). The molar ratio of the number of mol of alkylene oxide to the number of mol of bicyclic aliphatic alcohol (I') varies between 1 and 50 and more preferably between 1 and 10.

The reaction is then carried out in the presence of an effective amount of a catalyst.

Preferred catalysts which may be mentioned are strong bases and more particularly alkali metal or alkaline earth metal hydroxides, preferably sodium hydroxide or potassium hydroxide, or quaternary ammonium hydroxides, especially tetramethylammonium hydroxide, and alkali metal or alkaline earth metal alkoxides, preferably sodium or potassium methylate, ethylate or tert-butylate.

Primary, secondary or tertiary amines, preferably aliphatic amines, can also be used as catalysts, it being possible for these amines to contain other groups such as ether groups.

N,N-Dimethyllaurylamine may be mentioned as an example of an amine.

Catalysts of the Lewis acid type can be used as other types of catalysts. Examples of totally suitable catalysts which may be mentioned are $BF_3$ in the gaseous form or in solution in diethyl ether, tin chloride, $SnCl_4$, or antimony chloride, $SbCl_5$.

The amount of catalyst to be used is determined according to the nature of the catalyst.

In the case of a basic catalyst, this amount is expressed by the base number, which is defined as the amount of base, expressed in mg, relative to the weight of final product.

According to the invention, the base number is between 0.5 and 40 mg and preferably between 0.5 and 5 mg.

In the case of an acid catalyst, the amount used represents 0.1 to 10 mmol per mol of bicyclic aliphatic alcohol (I').

The reaction temperature is chosen so as to be sufficient to enable the reaction to be accomplished.

The reaction temperature is preferably chosen above 100° C., preferably between 120° and 250° C. and particularly preferably between 150° and 200° C.

The reaction is advantageously carried out in the presence of an inert gas, which can be nitrogen, a rare gas, preferably argon, or carbon monoxide.

The reaction takes place under atmospheric pressure or at a lower or higher pressure. Thus the reaction can be carried out under reduced pressure, for example at between 200 and 700 mm of mercury ($2.7.10^4$ to $9.3.10^4$ Pa), or under excess pressure, it being possible for the pressure to be between 1 and 4 bar.

In general, it is preferable to work under a positive pressure of between 1 and 4 bar and under nitrogen.

From a practical point of view, the process according to the invention is simple to carry out.

A preferred mode of carrying out this process consists in charging the bicyclic aliphatic alcohol (I') and establishing the inert gas atmosphere.

The first step is to dehydrate the reaction medium through elimination of the volatiles by heating to between 120° C. and 150° C.

The reaction medium is heated to the desired temperature of between 150° C. and 200° C.

The (Wop and/or Woe) reactant, e.g. the alkylene oxide, is then introduced under an inert atmosphere or under reduced pressure.

In the case where a mixed compound is prepared which is both polyethoxylated and polypropoxylated, the different kinds of alkylene oxide are introduced successively to give a configuration made up of block units. If it is intended to obtain a configuration made up of random units, all the alkylene oxides are incorporated at the same time.

At the end of the reaction, a neutralization step is carried out so as to bring the pH of the product obtained to between 5 and 8 and preferably to between 6 and 7.

This gives the aliphatic derivative (I') carrying a polyalkoxylated ring. The product obtained is in the form of a liquid and/or in the form of a paste.

If the catalyst used is basic, the neutralization is effected with any kind of acid, preferably with acetic acid.

In the case of an acid catalyst, the neutralization is effected with a base, preferably with sodium hydroxide or sodium carbonate or bicarbonate.

If it is desired to remove the catalyst from the product obtained, this is done by the traditional techniques, especially by treatment with a reagent which makes it possible to convert the catalyst to an insoluble salt; this is then removed by the conventional solid/liquid separation techniques, especially by filtration.

It should be noted that the molar ratio of the reactants (I') and (Wop and Woe) to the parameters p and q is easily determined by those skilled in the art as a function of the product which it is desired to obtain (especially a block or random polymer).

Referring to the compounds (I''), which are precursors of the compounds (Ib)—[m=0], Z=$Z_3$—, one of the processes for their preparation consists essentially of a condensation reaction between at least one bicyclo[a.b.c]-n-alk-1-enyl (where n=1 to 6 and a+b+c=5) and at least one diol, said condensation reaction advantageously being carried out in the absence of a solvent and, if appropriate, in the presence of a catalyst.

An example which may be mentioned is the case of the preparation of arbanol (isopropoxycamphane or 2-(isobornyloxy)isopropanol) by a known synthetic process involving the reaction of propylene glycol with camphene, as described in SANYO patent application JP-A-620 331 35 of 13th Feb. 1987 or patent US-A-3 354 225. To obtain Ib=I.1, the arbanol is then brought into contact with Wop= e.g. propylene oxide and Woe=e.g. ethylene oxide.

The optional functionalization which may follow can be for example an etherification or an esterification of the terminal hydrogen $R^6$ in formula (I). This step is performed in conventional manner known per se. It should be noted that if this functionalization is carried out, the neutralization is preferably carried out first.

Various possible ways of functionalizing the terminal hydrogen by a radical $R^6$ are given below as examples, without implying a limitation.

ether sulfates: $R_6=SO_3M$:

This makes it possible significantly to improve the properties of the products, in particular the wetting power and detergent power. The products are insensitive to the hardness of the water. The products are less irritant than the corresponding alkylsulfates.

The synthesis is performed in conventional manner by using reagents such as sulfur trioxide, sulfuric acid or oleum, chlorosulfonic acid or sulfamic acid. It will be preferable to use complexes of sulfur trioxide, in particular with Lewis bases such as pyridine, dioxane and sulfamic acid.

The reaction is carried out under conditions known to those skilled in the art, as described in PROCTER & GAMBLE, GB 1 111 208 (1968) and GAF, U.S. Pat. No. 3,392,185 (1968).

The products can be obtained in the form of alkali metal or ammonium salts after neutralization of the sulfuric acid hemiester with an appropriate base.

ether phosphates: $R^6=OPO_3M$:

These products are prepared when good solubilities in an electrolyte medium are desired.

This property is important, in particular for detergency applications.

Different phosphatization methods can be employed using such reagents as phosphoric acid, phosphorus pentoxide, phosphorus oxychloride or polyphosphoric acid, as described in GAF, U.S. Pat. No. 3,331,896 (1967). The resulting products have a high chemical stability and are particularly valued as dispersants.

ether carboxylates: $R^6=(CH_2)_n$—COONa, where n=1 or 2:

These products have a good solubility in a caustic medium and an excellent stability to electrolytes. The detergent power at high temperature is greatly increased and the products have antiredeposition properties, enabling them to be applied in textile treatment.

These products can be prepared in two ways:

for n=1, the product is brought into contact with the appropriate salts of monochloroacetic acid in the presence of sodium hydroxide at temperatures of about 50°–55° C. according to a procedure known to those skilled in the art, for example such as SANDOZ, U.S. Pat. No. 2,623,900;

for n=2, acrylic acid derivatives are used, as described in ARCHER, U.S. Pat. No. 2,983,738.

ether sulfonates: $R_6=(CH_2)_l$—$SO_3M$, where l=2 or 3:

This makes it possible to increase the heat stability of the products, and the compatibility with saline media enables them to be applied in the fields of petroleum and public works.

For l=2, two preparative procedures can be envisaged:

The corresponding chlorinated derivative is prepared by treatment with thionyl chloride. This chlorinated derivative is then treated with an alkali metal hydrogensulfite solution according to ROHM & HAAS, U.S. Pat. No. 2,115,192 (1938).

The product can also be prepared by a procedure which does not generate salts, such as treatment with sodium vinylsulfonate in the presence of alkali metal hydroxides according to STORK, U.S. Pat. No. 4,978,780.

For l=3, a treatment with propanesulfone is carried out according to K. SUGA, Austr. J. Chem., 21, 2333 (1968).

$R_6$=chlorinated or alkyl ethers:

Apart from their high stability in alkaline media, these derivatives are particularly valued for their excellent detergent power above their cloud point.

These products possess low foaming powers, making them suitable for applications of the bottle cleaning and detergency type, in particular for washing clothes.

In the case of chlorinated ethers, the products are prepared by treatment with thionyl chloride in the presence of alkali metal hydroxides according to ROHM & HANS, U.S. Pat. No. 2,817,686.

When $R_6=C_1-C_4$-alkyl or -alkylphenyl, the products are prepared by treatment with the corresponding alkyl or alkylphenyl halide. Benzyl chloride is preferably used as the alkylphenyl halide according to ROHM & HAAS, U.S. Pat. No. 2,913,416.

According to other features, the invention relates to the applications of the compounds (I), (Ia) and (Ib) described above.

Thus the invention further relates to a surfactant composition comprising at least one of these compounds (I).

Advantageously, the surfactant power of such a surfactant composition is adjustable via the parameters p and q in formula (I).

The present invention therefore further relates, but without implying a limitation, to detergent formulations containing this surfactant composition.

Such detergent formulations constitute concrete examples of exploitation of the advantageous characteristics of the compounds (I), namely:

these compounds (I) are derived from a renewable natural raw material, they have a low toxicity and no harmful effects on the environment, they have a low cost price, and they offer remarkable surfactant properties while at the same time not causing foam production and having a pleasant fragrant odor, which obviates the need for other expensive conventional fragrant additives.

The compounds (I) can be present in amounts of about 3 to 40% by weight in the detergent formulations according to the invention.

Detergent formulation is understood as meaning not only any powder or liquid detergent formulation intended for use in both washing machines and dishwashers and for household cleaning in general, but also any formulation which can be used for the cleaning/degreasing of metal surfaces and, more generally, of hard surfaces, e.g. steel plates.

Other additives of the type described below can be present in the detergent formulations in addition to the products of terpene origin of the invention.

Other SURFACTANTS, in amounts corresponding to about 3–40% by weight based on the detergent composition, i.e. surfactants such as:

ANIONIC SURFACTANTS:
alkyl ester sulfonates of the formula $R^{10}$—CH—$(SO_3M)$—$COOR^{11}$, where $R^{10}$ is a $C_8-C_{20}$-alkyl radical, preferably a $C_{10}-C_{16}$-alkyl radical, $R^{11}$ is a $C_1-C_6$-alkyl radical, preferably a $C_1-C_3$-alkyl radical, and M is an alkali metal cation (sodium, potassium, lithium), a substituted or unsubstituted ammonium cation (methyl-, di-methyl-, trimethyl-, tetramethyl-ammonium, di-methylpiperidinium, etc.) or a cation derived from an alkanolamine (monoethanolamine, di-ethanolamine, triethanolamine, etc.). very particular mention may be made of the methyl ester sulfonates in which the radical $R^{10}$ is $C_{14}-C_{16}$;

alkylsulfates of the formula $R^{12}OSO_3M$, where $R^{12}$ is a $C_{10}-C_{24}$-, preferably $C_{12}-C_{20}$- and very particularly $C_{12}-C_{18}$-alkyl or -hydroxyalkyl radical, M being a hydrogen atom or a cation as defined above, and the ethoxylated (EO) and/or propoxylated (PO) derivatives thereof containing an average of 0.5 to 6, preferably 0.5 to 3, units of EO and/or PO;

alkylamidesulfates of the formula $R^{13}CONHR^{14}$—$OSO_3M$, where $R^{13}$ is a $C_2-C_{22}$-alkyl radical, preferably a $C_6-C_{20}$-alkyl radical, and $R^{14}$ is a $C_2-C_3$-alkyl radical, M being a hydrogen atom or a cation as defined above, and the ethoxylated (EO) and/or propoxylated (PO) derivatives thereof containing an average of 0.5 to 60 EO and/or PO units;

salts of saturated or ,unsaturated $C_8-C_{24}$ fatty acids, preferably $C_{14}-C_{20}$ fatty acids, $C_9-C_{20}$-alkylbenzenesulfonates, primary or secondary $C_8-C_{22}$-alkylsulfonates, alkylglycerolsulfonates, the sulfonated polycarboxylic acids described in GB-A-1 082 179, paraffinsulfonates, N-acyl-N-alkyl-laurates, alkylphosphates, isethionates, alkylsuccinamates, alkylsulosuccinates, sulfosuccinate monoesters or diesters, N-acylsarcosinates, alkylglycosidesulfates and polyethoxycarboxylates, the cation being an alkali metal (sodium, potassium, lithium), a substituted or unsubstituted ammonium radical (methyl-, dimethyl-, tri- methyl-, tetramethyl-ammonium, dimethylpiperidinium, etc.) or a cation derived from an alkanolamine (monoethanolamine, diethanolamine, triethanolamine, etc.);

NON-IONIC SURFACTANTS:
polyalkoxylated (polyethoxylated, polypropoxylated, polybutoxylated) alkylphenols in which the alkyl substituent is $C_6-C_{12}$ and which contain from 5 to 25 alkylene oxide units; examples which may be mentioned are TRITON X-45, X-114, X-100 or X-102 marketed by THE ROHM & HAAS Company;

glucosamides, glucamides and glycerolamides;

polyalkoxylated $C_8-C_{22}$ aliphatic alcohols containing from 1 to 25 alkylene oxide (ethylene oxide, propylene oxide) units; examples which may be mentioned are TERGITOL 15-S-9 and TERGITOL 24-L-6 NMW marketed by UNION CARBIDE Corp., NEODOL 45-9, NEODOL 23-65, NEODOL 45-7 and NEODOL 45-4 marketed by THE SHELL CHEMICAL Company and KYRO EOB marketed by THE PROCTER & GAMBLE Company;

the products resulting from the condensation of ethylene oxide and the compound resulting from the condensation of propylene oxide with propylene glycol, such as the PLURONICS marketed by BASF;

the products resulting from the condensation of ethylene oxide and the compound resulting from the condensation of propylene oxide with ethylenediamine, such as the TETRONICS marketed by BASF;

amine oxides such as $C_{10}-C_{18}$-alkyldimethylamine oxides and $C_8-C_{22}$-alkoxyethyldihydroxyethylamine oxides;

the alkyl polyglycosides described in US-A-4 565 647;

$C_8-C_{20}$ fatty acid amides;

ethoxylated fatty acids;

ethoxylated fatty amides;

ethoxylated amines;

CATIONIC SURFACTANTS:
alkyldimethylammonium halides;

AMPHOTERIC AND ZWITTERIONIC SURFACTANTS:
alkyldimethylbetaines, alkylamidopropyldimethylbetaines, alkyltrimethylsulfobetaines and fatty acid/protein hydrolyzate condensation products.

BUILDERS, in amounts corresponding to about 5–50% by weight, preferably about 5–30% by weight, for the liquid detergent formulations, or to about 10–80% by weight, preferably 15–50% by weight, for the powder detergent formulations, i.e. builders such as:

INORGANIC BUILDERS:
  alkali metal, ammonium or alkanolamine polyphosphates (tripolyphosphates, pyrophosphates, orthophosphates, hexametaphosphates);
  tetraborates or borate precursors;
  silicates, in particular those with an $SiO_2/Na_2O$ ratio of the order of 1.6/1 to 3.2/1 and the sheet silicates described in US-A-4 664 839;
  alkali metal or alkaline earth metal carbonates (bicarbonates, sesquicarbonates);
  cogranulates of hydrated alkali metal silicates and alkali metal (sodium or potassium) carbonates rich in silicon atoms in the Q2 or Q3 form, described in EP-A-488 868;
  crystalline or amorphous alkali metal (sodium, potassium) or ammonium aluminosilicates such as zeolites A, P, X, etc.; zeolite A with a particle size of the order of 0.1–10 micrometers is preferred;

ORGANIC BUILDERS:
  water-soluble polyphosphonates (ethane 1-hydroxy-1, 1-diphosphonates, methylenediphosphonate salts, etc.);
  carboxylic polymers or copolymers or water-soluble salts thereof, such as:
    polycarboxylate ethers (oxydisuccinic acid and salts thereof, monosuccinic/tartaric acid and salts thereof, disuccinic/tartaric acid and salts thereof),
    hydroxypolycarboxylate ethers,
    citric acid and salts thereof and mellitic acid and succinic acid and salts thereof,
    salts of polyacetic acids (ethylenediaminetetraacetates, nitrilotriacetates, N-(2-hydroxyethyl)nitrilodiacetates),
    $C_5-C_{20}$- alkylsuccinic acids and salts thereof (2-dodecenylsuccinates, laurylsuccinates),
    carboxylic polyacetal esters,
    polyaspartic acid, polyglutamic acid and salts thereof;
    polyimides derived from the polycondensation of aspartic acid and/or glutamic acid;
    polycarboxymethylated derivatives of glutamic acid or other amino acids.

BLEACHING AGENTS, in amounts of about 0.1–20% by weight, preferably of about 1–10% by weight, optionally in combination with BLEACHING ACTIVATORS, in amounts of about 0.1–60% by weight, preferably about 0.5–40% by weight, i.e. bleaching agents and activators such as:

BLEACHING AGENTS:
  perborates such as sodium perborate monohydrate or tetrahydrate;
  peroxygen compounds such as sodium carbonate peroxyhydrate, pyrophosphate peroxyhydrate, urea peroxyhydrate, sodium peroxide and sodium persulfate, preferably in combination with a bleaching activator generating a carboxylic peroxyacid in situ in the detergent medium; among these activators there may be mentioned tetraacetylethylenediamine, tetraacetylmethylenediamine, tetraacetylglycoluril, sodium p-acetoxybenzenesulfonate, pentaacetyl glucose, octaacetyl lactose, etc.;
  percarboxylic acids and salts thereof (called "percarbonates") such as magnesium monoperoxyphthalate hexahydrate, magnesium metachloroperbenzoate, 4-nonylamino-4-oxoperoxybutyric acid, 6-nonylamino-6-oxoperoxycaproic acid, diperoxy-dodecanedioic acid, peroxysuccinic acid nonylamide and decyl-diperoxysuccinic acid.

These agents can be used in combination with at least one of the antisoiling or antiredeposition agents mentioned below.

Mention may also be made of non-oxygenated bleaching agents, which act by photoactivation in the presence of oxygen, i.e. agents such as sulfonated aluminum and/or zinc phthalocyanines.

ANTISOILING AGENTS, in amounts of the order of 0.01–10%, preferably about 0.1–5% and very particularly of the order of 0.2–3% by weight, i.e. agents such as:
  cellulose derivatives such as cellulose hydroxyethers, methyl cellulose, ethyl cellulose, hydroxypropyl methyl cellulose and hydroxybutyl methyl cellulose;
  polyvinyl esters grafted onto polyalkylene backbones, such as polyvinyl acetates grafted onto polyethylene oxide backbones (EP-A-219 048);
  polyvinyl alcohols;
  polyester copolymers based on ethylene terephthalate and/or propylene terephthalate and polyoxyethylene terephthalate units, with a molar ratio ethylene terephthalate and/or propylene terephthalate (number of units)/polyoxyethylene terephthalate (number of units) of the order of 1/10 to 10/1, preferably of the order of 1/1 to 9/1, the polyoxyethylene terehthalates having polyethylene oxide units with a molecular weight of the order of 300 to 5000, preferably of the order of 600 to 5000 (US-A-3 959 230, US-A-3 893 929, US-A-4 116 896, US-A-4 702 857, US-A-4 770 666);
  the sulfonated polyester oligomers obtained by sulfonating an oligomer derived from ethoxylated allyl alcohol, dimethyl terephthalate and 1,2-propylenediol, and containing from 1 to 4 sulfonated groups (US-A-4 968 451);
  polyester copolymers based on propylene terephthalate and polyoxyethylene terephthalate units and terminating with ethyl or methyl units (US-A-4 711 730) or polyester oligomers terminating with alkylpolyethoxy groups (US-A-4 702 857) or anionic sulfopolyethoxy groups (US-A-4 721 580) or sulfoaroyl groups (US-A-4 877 896);
  the polyester-polyurethanes obtained by reacting a polyester of number-average molecular weight 300–4000, obtained from adipic acid and/or terephthalic acid and/or sulfoisophthalic acid and a diol of molecular weight below 300, with a prepolymer containing terminal isocyanate groups, obtained from a polyoxyethylene glycol of molecular weight 600–4000 and a diisocyanate (FR-A-2 334 698).

ANTIREDEPOSITION AGENTS, in amounts of about 0.01–10% by weight for a powder detergent composition, or of about 0.01–5% by weight for a liquid detergent composition, i.e. agents such as:
  ethoxylated monoamines or polyamines and ethoxylated amine polymers (US-A-4 597 898, EP-A-11 984);
  carboxymethyl cellulose;
  the sulfonated polyester oligomers obtained by condensing isophthalic acid, dimethyl sulfosuccinate and diethylene glycol (FR-A-2 236 926);
  polyvinylpyrrolidones.

CHELATING AGENTS for iron and magnesium, in amounts of the order of 0.1–10% by weight, preferably of the order of 0.1–3% by weight, i.e. agents such as:

aminocarboxylates such as ethylenediaminetetraacetates, hydroxyethylethylenediaminetriacetates and nitrilotriacetates;

aminophosphonates such as nitrilotris(methylene phosphonates);

polyfunctional aromatic compounds such as dihydroxydisulfobenzenes.

POLYMERIC DISPERSANTS, in an amount of the order of 0.1–7% by weight, for controlling the calcium and magnesium hardness, i.e. dispersants such as:

water-soluble salts of polycarboxylic acids with a molecular weight of the order of 2000 to 100,000, obtained by polymerizing or copolymerizing ethylenically unsaturated carboxylic acids such as acrylic acid, maleic acid or anhydride, fumaric acid, itaconic acid, aconitic acid, mesaconic acid, citraconic acid or methylenemalonic acid, and very particularly polyacrylates with a molecular weight of the order of 2000 to 10,000 (US-A-3 308 067) and acrylic acid/maleic anhydride copolymers with a molecular weight of the order of 5000 to 75,000 (EP-A-66 915);

polyethylene glycols with a molecular weight of the order of 1000 to 50,000.

BRIGHTENERS, in an amount of about 0.05–1.2% by weight, i.e. brighteners such as:

derivatives of stilbene, pyrazoline, coumarin, fumaric acid, cinnamic acid, azoles, methinecyanines, thiophenes, etc. ("The production and application of fluorescent brightening agents"—M. ZAHARADNIK, published by John Wiley & Sons, New York, 1982).

FOAM SUPPRESSANTS, in an,mounts which can range up to 5% by weight, i.e. suppressants such as:

$C_{10}$–$C_{24}$ monocarboxylic fatty acids or alkali metal, ammonium or alkanolamine salts thereof, and fatty acid triglycerides;

saturated or unsaturated aliphatic, alicyclic, aromatic or heterocyclic hydrocarbons such as paraffins and waxes;

N-alkylaminotriazines;

monostearyl phosphates and monostearyl alcohol phosphates;

polyorganosiloxane oils or resins, optionally in combination with silica particles.

SOFTENERS, in amounts of about 0.5–10% by weight, i.e. softeners such as clays.

ENZYMES, in an amount which can range up to 5 mg by weight, preferably of the order of 0.05–3 mg of active enzyme/g of detergent composition, i.e. enzymes such as:

proteases, amylases, lipases, cellulases and peroxydases (U.S. Pat. No. 3 553 139, U.S. Pat. No. 4 101 457, U.S. Pat. No. 4 507 219, U.S. Pat. No. 4 261 868).

OTHER ADDITIVES such as:

alcohols (methanol, ethanol, propanol, isopropanol, propanediol, ethylene glycol, glycerol);

buffers;

perfumes;

pigments.

The products of terpene origin of the invention can also be used as industrial cleaning agents for metal surfaces.

It has furthermore been seen that the compounds of formula (I) emit a varied and very interesting range of odors.

Thus e.g. the olfactory performance characteristics of the NOPOL derivatives (Ia) defined above are evaluated on solutions of the products in ethanol or diethyl phthalate (10% by weight).

| p | q | FAMILY | NOTE | OLFACTORY DESCRIPTION |
|---|---|---|---|---|
| 0 | 3.3 | citrus fruits | top/heart | woody, fresh, spicy, ginger |
| 2 | 0.0 | hesperidic | top/heart | very fresh, lemon, thyme, wild type |
| 2 | 3.3 | hesperidic | top/heart | very waxy, very woody, oily |
| 2 | 5.1 | hesperidic | top | lemon-scented, very fresh, wood, eau de cologne |
| 2 | 7.5 | hesperidic | top/heart | lemon-scented, wax, woody |
| 2 | 10.5 | hesperidic | top/heart | piquant, lemon-scented, woodland berries |

The respective ratios of the parameters p and q of the radicals (Wop) and (Woe) in formula (I) enable the olfactory performance characteristic to be adjusted to the desired application.

The great advantage of the products (I) according to the invention over the conventional perfume components is that these products (I) are all soluble in water, which greatly simplifies their formulation without requiring the use of organic solvents.

By virtue of their olfactory performance characteristics, the products of the invention can be used as fragrant ingredients in fragrant compositions and perfume substances and products.

"Fragrant compositions" are understood as denoting mixtures of various ingredients, such as solvents, solid or liquid carriers, fixatives, various odoriferous compounds, etc., into which at least one of the compounds of formula (I) is incorporated. The latter are used to impart the desired fragrance to various types of finished products.

Perfume bases constitute preferred examples of fragrant compositions in which the compounds of formula (I) can advantageously be used.

Eaux de toilette, after-shave lotions, perfumes, soaps, bath or shower gels or deodorant or antiperspirant products, whether in stick or lotion form, constitute examples of substances or finished products to which the compounds of formula (I) impart their original note.

They can also be used in shampoos and in all types of hair product.

They can also perfume talcs or powders of any kind.

They are also suitable for air fresheners or any household cleaning materials.

The amount of the compound of formula (I) in the fragrant compositions according to the invention, expressed as the percentage by weight in the composition in question, depends on the nature of said composition (perfume base or eau de toilette, for example) and on the potency and nature of the desired effect in the final product. It is self-evident that in a perfume base, the amount of the compound of formula (I) can be very substantial, for example more than 50% by weight, and can be as much as 90% by weight, whereas in a perfume, an eau de toilette or an after-shave lotion, this amount may be very much less than 50% by weight.

The compound of formula (I) can also be used in perfumed shampoos in an amount of 0.5 to 2% or for perfuming any hair product.

Thus the lower limit of the amount of the compound of formula (I) can be that which modifies the fragrance or note of the finished product in a manner perceptible to the smell. In some cases, this minimum amount can be of the order of 0.01% by weight. It is obviously possible to use amounts not included within the limits indicated above, without thereby going outside the framework of the present invention.

In view of the fact that the compounds according to the invention possess the dual function of surfactant and perfume, it is possible to envisage providing, as an application of said compounds, a surfactant and fragrant composition which comprises at least one such compound.

It is self-evident that the above-described detergent formulations according to the invention can comprise, in addition to or instead of the surfactant composition based on (I), the fragrant composition based on (I) and/or the surfactant and fragrant composition based on (I).

The following Examples will provide a clearer understanding of the present invention and will make it possible to illustrate all its advantages and its practical variants.

EXAMPLES

1ST PART: PREPARATION AND SURFACTANT PROPERTIES OF THE COMPOUNDS ACCORDING TO THE INVENTION

Example 1
Synthesis of NOPOL=Precursor (I')
EXPERIMENT 1:

Paraformaldehyde (1.19 g, 39.6 mmol), toluene (10 ml) and zinc chloride (0.12 g, 0.88 mmol) are introduced successively into a 100 ml reactor. The mixture is heated to 105° C. and β-pinene (7.08 g, 52 mmol) is introduced over 20 minutes.

The temperature is maintained at 105° C. for two hours. The assay by gas chromatography indicates a 51% degree of conversion of the β-pinene and a 62% selectivity in terms of NOPOL.

EXPERIMENT 2:

β-Pinene (7.11 g, 52.3 mmol) and paraformaldehyde (1.62 g, 54 mmol) are introduced into a 100 ml TEFLON autoclave. The mixture is heated under autogenous pressure at 180° C. for 1 hour.

The assay by gas chromatography indicates a 59% degree of conversion of the β-pinene and a 99% selectivity in terms of NOPOL.

Example 2
Preparation of Compounds of Formula (Ia) of the Polyethoxylated and/or Polypropoxylated Type The principle of this preparation consists in carrying out a condensation reaction between 6,6-dimethylbi-cyclo[3.1.1]hept-2-en-2-ethanol=NOPOL and ethylene oxide and/or propylene oxide. The NOPOL used is that marketed by FLUKA. Its purity is greater than 98% and its water content is 0.37% (Karl Fischer).

In the present Example, the following eight compounds (Ia) are synthesized (EO=ethylene oxide, PO=propylene oxide).

2.1 NOPOL 3.3 EO:

NOPOL (2 kg, 12 mol) and an aqueous solution of potassium hydroxide (50%, 7.4 g) are introduced into a 5-liter ethoxylation reactor.

The reaction medium is dehydrated at 120° C. under a stream of nitrogen.

It is then heated to 165° C. and the ethylene oxide is introduced (1.75 kg, 3.3 mol equivalents).

The reaction medium is then cooled and neutralized by the addition of acetic acid until the pH is 7. The liquid obtained is filtered on an absorbent earth (Clarcel DIC).

This gives a pale yellow fluid liquid.

2.2 NOPOL 5.1 EO:

NOPOL (1.5 kg, 9 mol) and an aqueous solution of potassium hydroxide (50%, 7 g) are introduced into a 5-liter ethoxylation reactor. The reaction medium is dehydrated at 120° C. under a stream of nitrogen.

It is then heated to 165° C. and the ethylene oxide is introduced (2.02 kg, 5.1 mol equivalents). The reaction medium is then cooled and neutralized by the addition of acetic acid until the pH is 7. The liquid obtained is filtered on an absorbent earth (Clarcel DIC).

This gives a pale yellow fluid liquid.

2.3 NOPOL 7.5 EO:

The procedure is as for NOPOLS 3.3 EO and 5.1 EO.

2.4 NOPOL 2 PO:

NOPOL (2 kg, 12 mol) and an aqueous solution of potassium hydroxide (50%, 6.7 g) are introduced into a 5-liter ethoxylation reactor.

The reaction medium is dehydrated at 120° C. under a stream of nitrogen.

It is then heated to 170° C. and the propylene oxide is introduced (0.743 kg, 2 mol equivalents). The reaction medium is then cooled and neutralized by the addition of acetic acid until the pH is 7. The liquid obtained is filtered on an absorbent earth (Clarcel DIC).

This gives a pale yellow fluid liquid.

2.5 NOPOL 2 PO/3.3 EO:

NOPOL (1 kg, 6 mol) and an aqueous solution of potassium hydroxide (50%, 3.1 g) are introduced into a 5-liter ethoxylation reactor.

The reaction medium is dehydrated at 120° C. under a stream of nitrogen.

It is then heated to 170° C. and the propylene oxide is introduced (0.7 kg, 2 mol equivalents). When the addition of the propylene oxide is complete, the ethylene oxide is introduced (0.87 kg, 5.7 mol equivalents).

The reaction medium is then cooled and neutralized by the addition of acetic acid until the pH is 7. The liquid obtained is filtered on an absorbent earth (Clarcel DIC).

This gives a pale yellow fluid liquid.

2.6 NOPOL 2 PO/5.1 EO:

NOPOL (1 kg, 6 mol) and an aqueous solution of potassium hydroxide (50%, 3.7 g) are introduced into a 5-liter ethoxylation reactor.

The reaction medium is dehydrated at 120° C. under a stream of nitrogen.

It is then heated to 170° C. and the propylene oxide is introduced (0.7 kg, 2 mol equivalents). When the addition of the propylene oxide is complete, the ethylene oxide is introduced (1.35 kg, 5.1 mol equivalents).

The reaction medium is then cooled and neutralized by the addition of acetic acid until the pH is 7. The liquid obtained is filtered on an absorbent earth (Clarcel DIC).

This gives a pale yellow fluid liquid.

2.7 NOPOLS 2 PO/7.5 EO and 2 PO/10.3 EO:

The procedure is as for NOPOLS 2 PO/3.3 EO and 2 PO/5.1 EO.

2.8 CHEMICAL ANALYSIS:

The chemical analysis (hydroxyl number and base number determined on the crude condensation products of the reaction) gave the following results:

|  | $N_{OH}$ found | Theoretical $N_{OH}$ | $N_B$ |
|---|---|---|---|
| NOPOL | 317.8 | 337.5 | — |
| NOPOL 0.3 EO | 180.9 | 177.2 | 0.90 |
| NOPOL 5.1 EO | 145.0 | 143.4 | 0.70 |
| NOPOL 7.5 EO | 113.0 | 113.0 | 1.60 |
| NOPOL 2 PO | 212.8 | 198.7 | 1.01 |
| NOPOL 2 PO/3.3 EO | 143.5 | 130.8 | 0.60 |
| NOPOL 2 PO/5.1 EO | 117.8 | 110.8 | 0.55 |
| NOPOL 2 PO/7.5 EO | 90.2 | 91.1 | 1.15 |

- Base number $N_B$: obtained by potentiometry and expressed in milligrams of potassium hydroxide per gram of crude product.
- Hydroxyl number $N_{OH}$: obtained by the acetylation method as typically described in R. STETZLER, Anal. Chem., 34, 194 (1962).

Example 3
Properties of the NOPOLS EO and/or PO
3.1 CLOUD POINTS:

This measurement makes it possible to assess the surfactant properties of the NOPOLS prepared as indicated above in Example 1.

| | CLOUD POINT (°C.) | | | |
|---|---|---|---|---|
| | BDG | | 0.5% DW | |
| n | NOPOL 2 PO + n EO | NOPOL n EO | NOPOL 2 PO + n EO | NOPOL n EO |
| 3.3 | 55.7 | 56.9 | — | — |
| 5.1 | 65.5 | 70.2 | <5 | <5 |
| 7.5 | 74.9 | 80.6 | 53 | 66.8 |
| 10.3 | 81.0 | — | 77 | — |

- BDG = butyl diglycol
- DW = distilled water

3.2 COMPARISON WITH ETHOXYLATED ALCOHOLS AND NONYLPHENOLS:

a) NOPOL 3.3 EO (HLB 9.4) and NOPOL 5.1 EO (HLB 11.5):

These two products are compared with:
the range of ethoxylated $C_{12}/C_{14}$ alcohols (LA 20, LA 30 and LA 40),
the range of ethoxylated nonylphenols (NP 3, NP 4, NP 5, NP 6 and NP 7).

At the same HLB, the cloud points of the ethoxylated NOPOLS 3.3 and 5.1 are well below those of the ethoxylated alcohols and approximately equal to those of the ethoxylated nonylphenols.

FIG. 1 attached shows the curves of the measured cloud points as a function of the HLB. The measurements are made at concentrations of 10% in 25% aqueous BDG.

b) NOPOL 7.5 EO (HLB 13.3):

The same observation as above is made when comparing this product with:
the ethoxylated nonylphenols (NP 8, NP 9, NP 10, NP 1064 and NP 12),
the ethoxylated alcohol $C_{12}$–$C_{14}$-9 EO (LA 90),
the ethoxylated alcohol $C_{10}$–$C_{12}$-5.2 EO (DB 311).

Figure 2:
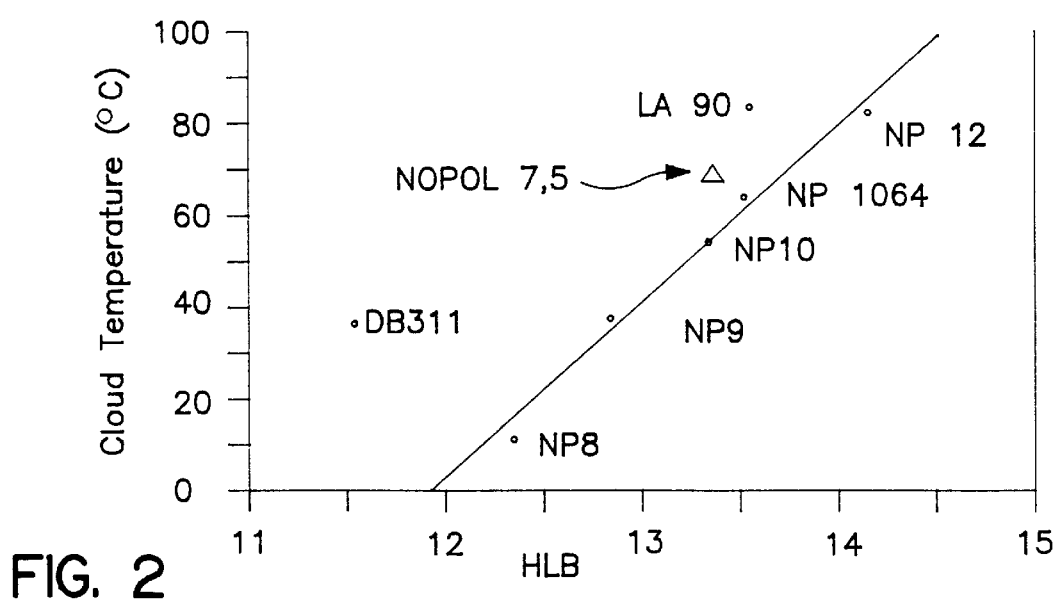
Figure 3:
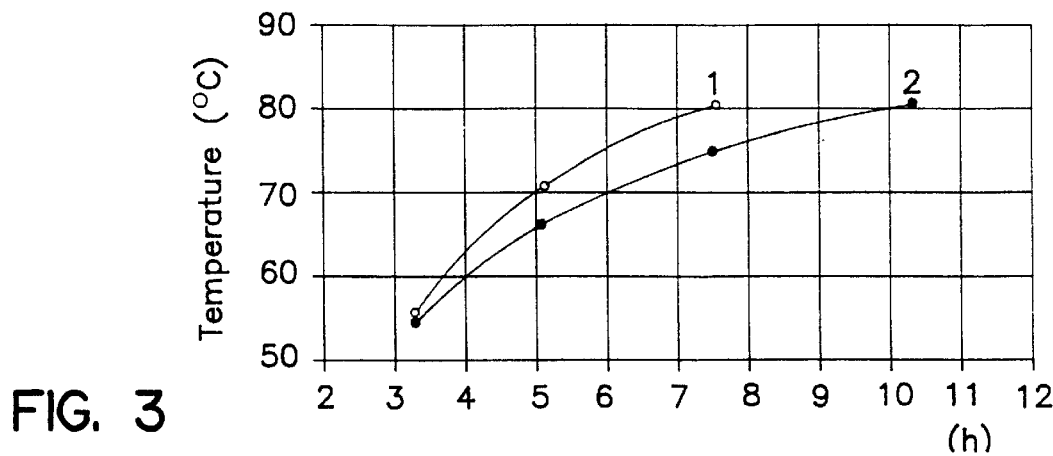

FIG. 2 attached shows the curves of the measured cloud points as a function of the HLB. The measurements are made at concentrations of 5 g/liter of distilled water.

c) NOPOLS n EO and 2 PO/n EO:

The change in the cloud point as a function of n is shown in FIG. 3 attached:
curve 1=NOPOL n EO
curve 2=NOPOL 2 PO/n EO The measurements are made at concentrations of 10% in 25% aqueous BDG.

2ND PART: DETERGENCY

The terpene products of the invention can also be used as industrial cleaning agents for metal surfaces. The method of measuring the detergent power of the terpene products of the invention was performed as follows:

DETERGENT POWER:
PRINCIPLE:

The test simulates a simplified machine wash using a tergotometer. It consists in washing soiled fabric samples at 40° C. in a standard and uniform manner with only the test product and sodium bicarbonate to stabilize the pH. The wash lasts for thirty minutes and the detergency is evaluated by measuring the whiteness of the pieces of fabric, before and after washing, using a calorimeter.

EQUIPMENT, FABRICS AND PRODUCTS:
EQUIPMENT:

Tergotometer: "U.S. TESTING Co. Inc.", HOBOKEN N.J., Model 7243
Rolling machine for ironing the fabric samples after washing
Color-measuring apparatus: "Dr Lange LUCI 100"

FABRICS:

The standard fabrics are manufactured by CFT (Center For Test materials) or by the Company "Test Fabric". They have the following characteristics:

| | (soil) | number of pieces per test |
|---|---|---|
| Standard soiled fabrics | | |
| Soiled cotton CS-3 CFT | (wine) | 2 |
| Soiled cotton K 10D CFT | (mineral oil and carbon black) | 2 |
| Soiled cotton AS-2 CFT | (mineral oil and carbon black) | 2 |
| Polyester cotton E MPA 104 CFT | (mineral oil and carbon black) | 2 |
| Polyester Dacron type 54 Test Fabric | (mineral oil and carbon black) | 2 |
| Standard white fabrics | | |
| Cotton CN 1, white, non-soiled, from CFT | | 5 |
| Polyester cotton PCN 1, white, non-soiled, from CFT | | 5 | i.e. a total of 20 pieces of fabric for each test.

PRODUCTS:

"LABS", technical-grade sodium dodecylbenzenesulfonate (ALDRICH), is the control product taken as a reference.

PROCEDURE:
DETERGENCY TEST:

The tergotometer is an apparatus consisting of four 2-liter stainless steel pots fitted with stirrers which are adjusted to 50 cycles per minute (100 to-and-fro movements). The pots are placed in a tank of water regulated at 40° C.

1 liter of softened water containing:
1 gram of surfactant
1 gram of sodium bicarbonate is placed in each pot.

When the water has reached the requisite temperature, the pots are introduced into the thermostated bath, the stirring and a chronometer being started simultaneously.

When washing has ended (30 minutes), the baths are recovered (250 cc) for a pH check.

The fabrics are rinsed three times with tap water and then squeezed out by hand and individually dried flat between two sheets of white absorbent paper.

The fabrics are again placed between two clean sheets of absorbent paper and ironed in the rolling machine at a temperature of about 110° C.

COLOR MEASUREMENT:

The measurements are made with the "LUCI 100" calorimeter, before and after washing, according to the system "L", "a", "b" (scale of black to white, green to red and blue to yellow), in order to measure the detergent power of the surfactants tested (increase in the whiteness of the soiled pieces of fabric).

CALCULATION OF THE DETERGENCY:

The value "DE" (detergency) is calculated for each type of fabric as the geometric sum of the color differences DL, Da and Db on the soiled fabrics before and after washing.

Let detergency $DE = (DL^2 + Da^2 + Db^2)^{1/2}$.

Example 4

| po (p) | EO (q) | |
|---|---|---|
| 2 | 3.3 | product 1 |
| 2 | 5.1 | product 2 |
| 2 | 7.5 | product 3 |
| 2 | 10.3 | product 4 |

The detergent power is measured according to the detergency test described above (simulated wash using a tergotometer): the cumulative detergency, measured on the different types of fabric, gives the following results, taking LABS as the reference with a detergency "DE" of 100.

| | "DE" |
|---|---|
| LABS | 100 |
| conventional mixture of non-ionic surfactants for detergent compositions, consisting of $C_{13}$ fatty alcohol ethoxylated with 3 EO + $C_{13}$ fatty alcohol ethoxylated with 9 EO in the weight ratio 30/70 | 96 |
| product 2 | 89 |
| mixture of products 1 + 2 + 3 + 4 in the ratio 10/50/20/20 | 94 |

Example 5: Use of the Mixture of Products 1+2+3+4 in a Concentrated Detergent Formulation For Washing Clothes

| | |
|---|---|
| Linear sodium alkylbenzenesulfonate | 3% |
| Products 1 + 2 + 3 + 4 (10/56/20/20) | 8% |
| NABION 15 ® (carbonate/silicate cogranulate marketed by RHONE-POULENC) | 40% |
| Perborate tetrahydrate | 16% |
| Sodiuiu carboxymethyl cellulose | 0.6% |
| Enzyines (savinase/alkalase) | 0.6% |
| Mixture of optical brighteners | 0.14% |
| Tetraacetylethylenediamine (perborate activator) | 4.3% |
| Sodium salt of hydroxyethylene-1,1-diphosphonate | 1.6% |
| SOKALAN CP5 ® (acrylic/maleic copolymer marketed by BASF) | 5% |
| Absorbent light sodium carbonate | 6% |
| Solid silicone antifoam containing 8% of silicone | 2.5% |
| Perfume | 0.12% |
| Sodium sulfate | ad 100% |

Example 6: Use of the Mixture of Products 1+2+3+4 in a Detergent Formulation for Washing Clothes

| | |
|---|---|
| Linear sodium alkylbenzenesulfonate | 7.5% |
| Products 1 + 2 + 3 + 4(10/50/20/20) | 4.5% |
| Zeolite TEL | 24% |
| Disilicate ALNA | 2.5% |
| Perborate tetrahydrate | 14% |
| Sodium carboxymethyl cellulose | 0.6% |
| Enzymes (esterase) | 0.3% |
| Mixture of optical brighteners | 0.11% |
| Tetraacetylethylenediainine (perborate activator) | 2% |
| Sodium salt of hydroxyethylene-1,1-diphosphonate | 1.6% |
| SOKALAN CP5 ® (acrylic/maleic copolymer marketed by BASF) | 4% |
| Sodium carbonate | 14% |
| Antifoam | 1.5% |
| Repell-O-Tex ® (antisoiling agent marketed by RHONE-POULENC) | 0.1% |
| Perfume | 0.1% |
| Sodium sulfate | ad 100% |

Example 7: Degreasing Formulation for S Metal Sheets, Based on NOPOL 5.1 EO

| | |
|---|---|
| NOPOL 5.1 EO | 5% |
| MIRANOL J2M Conc. (disodium caprylamphodiacetate) | 11.7% |
| Triethanolamine | 5% |
| Butyl diglycol | 5% |
| NERVANAID NTA Na3 (sodium nitrilotriacetate marketed by Rhone-Poulenc) | 10% |
| Perfume and color | |
| Water | ad 100% |

This formulation is diluted 10- to 100-fold.

Example 8: Degreasing of Metal Sheets Using Formulations Containing the Compounds (Ia) According to the Invention: Detergency Test 8.1 PROCEDURE:

The test comprises three steps:

1) GREASING of predegreased steel plates of trademark "Q-Panel". Stock no. R-36, type "Dull matt finish" of 0.8×76×152 mm.

The plates are immersed for 2 minutes in the oils to be tested and are then hung for 24 hours to drain.

2) CLEANING:

The greased plates are immersed at 50° C. in a detergent solution made up by dilution of the base detergent "PARCO 8805" (PARKER) to 20 g/l and containing 1 g/l (active substance) of the surfactant to be tested. The tests are performed in softened water.

3) RINSING AND SCORING:

The plates are rinsed under a thin trickle of water for 5 seconds on each side (flow rate=2 1/min; temperature between 15° and 17° C.). They are scored from 0 to 4 according to the proportion of surface covered with a continuous film of water, i.e. the proportion of surface devoid of all traces of residual oil.

"0" corresponds to a total absence of wetting.

"4" corresponds to a perfect wetting of the whole plate on both sides (see annexes).

The immersion time of the plate in the detergent solution is chosen so as to permit a complete degreasing (score 4) with the reference product (IGEPAL NP 10) and an absence of degreasing (score 0) with the detergent solution containing only the diluted base detergent and no additional surfactant.

The oils used are:
  the paraffin oil TOTALS 200 Neutral. The immersion time of the plate in the detergent solution is 1 minute.
  a triglyceride, namely the colza oil PHYTOROB® PHT, which is difficult to remove. The procedure followed comprises five washing and rinsing steps for a total immersion time of 15 minutes. This immersion time is (theoretically) necessary for achieving complete cleaning of the plate with the reference IGEPAL® NP 10.

8.2 SURFACTANTS TESTED:

Detergent PARCO 8805 from PARKER, by itself (without surfactant) [concentrated solution (solids content 45%) diluted to 20 g/l]

IGEPAL® NP 10 [nonylphenol containing 10 ethylene oxides]

PLURAFAC® LF 431 from BASF [CH₃ blocked alcohol EO/PO]

NOPOL 7.5 EO+5.5 PO [compound Ia]

NOPOL 7.5 EO [compound Ia]

NOPOL 2 PO+3.3 EO [compound Ia]

NOPOL 2 PO+5.1 EO [compound Ia]

NOPOL 2 PO+7.5 EO [compound Ia]

NOPOL 2 PO+10.3 EO [compound Ia]

The compounds (Ia) are prepared as described in the foregoing Examples.

8.3 DETERGENCY IN RESPECT OF PARAFFIN OIL:

The immersion time of the plate in the detergent solution is 1 minute.

TABLE 1

METALLURGICAL DEGREASING AT 50° C.
PARAFFIN OIL 200 NEUTRAL®

| Detergent (20 g/l) + surfactant (1 g/l) | 1 min score |
|---|---|
| Detergent PARCO 8805 by itself | 0 |
| IGEPAL NP 10 | 4 |
| NOPOL 7.5 EO | 4 |
| NOPOL 7.5 EO + 5.5 PO | 4 |
| NOPOL 2 PO + 3.3 EO | 3 |
| NOPOL 2 PO + 5.1 EO | 3+ |
| NOPOL 2 PO + 7.5 EO | 4 |
| NOPOL 2 PO + 10.3 EO | 4 |
| PLURAFAC LF 431 | 4 |

The detergent by itself is unable to degrease the plates covered with 200 NEUTRAL oil. By contrast, the result is excellent with 1 g/l of IGEPAL NP 10 and PLURAFAC LF 431. NOPOLS 7.5 EO and 7.5 EO+5.5 PO are also excellent. In the NOPOL 2 PO series, it is preferable to have at least 7.5 ethylene oxides in order to achieve perfect degreasing after 1 minute.

8.4 DETERGENCY IN RESPECT OF COLZA OIL: The immersion time in the detergent solution is 15 minutes.

The detergent by itself gives no result after this time. By contrast, IGEPAL NP 10 totally degreases the Q-Panel plate after 10 minutes of immersion.

TABLE 2

METALLURGICAL DEGREASING AT 50° C.
COLZA OIL

| DETERGENT (20 g/l) + SURFACTANT (1 g/l) | SCORE | | | | |
|---|---|---|---|---|---|
| | 1 min | 2 min | 5 min | 10 min | 15 min |
| Detergent PARCO 8805 by itself | 0 | 0 | 0 | 0 | 0 |

TABLE 2-continued

METALLURGICAL DEGREASING AT 50° C.
COLZA OIL

| DETERGENT (20 g/l) + SURFACTANT (1 g/l) | SCORE | | | | |
|---|---|---|---|---|---|
| | 1 min | 2 min | 5 min | 10 min | 15 min |
| IGEPAL NP 10 | 0 | 1 | 2 | 4 | |
| NOPOL 7.5 EO + 5.5 PO | 0 | 1 | 1 | 2 | |
| NOPOL 2 PO + 3.3 EO | 0 | 0 | 0 | 0 | |
| NOPOL 2 PO + 5.1 EO | 0 | 0 | 1 | 1+ | 2+ |
| NOPOL 2 PO + 7.5 EO | 0 | 1 | 2 | 2+ | 3 |
| NOPOL 2 PO + 10.3 EO | 0 | 1 | 1+ | 1+ | 2 |
| PLURAFAC LF 431 | 0 | 1 | 1+ | 1+ | 2 |

Among the ethoxylated NOPOLS, the best product is NOPOL 2 PO+7.5 EO, which achieves a score of 3.

The product PLURAFAC LF 431 is not the best detergent for colza oil.

EXAMPLE 9: EVALUATION OF NOPOL DERIVATIVES (Ia) -FOAMING TEST 9.1 OPERATING CONDITIONS:

The test used is as follows:

The surfactant solution (weight=900 g) is stirred with a centripetal blade at 2000 rpm for 5 min. The stirring turbine has a diameter of 40 mm. The change in the volume of foam is plotted as a function of time.

The cloud points of the basic solutions are determined.

The NOPOL derivatives tested are: NOPOL 2 PO+5.1 EO and NOPOL 2 PO.

In a basic medium, NOPOL 2 PO+5.1 EO and NOPOL 7.5 EO+5.5 PO produce absolutely no foam at 20° C. or at 50° C.

The products used are:

ANTAROX® BL 330 (chlorinated blocked ethoxylated alcohol)

IGEPAL® NP 1064 (ethoxylated nonylphenol containing 10 EO)

IGEPAL® NP 9 (ethoxylated nonylphenol containing 9 EO)

PLURAFAC® LF 431 (BASF) (phosphate ester)

TETRONIC 701

SAPONINE (PROLABO)

The detergent power of the NOPOLS used is at least as good as that of the controls.

9.2 FOAMING POWER IN A BASIC MEDIUM AT 20° C. AND 50° C.:

TEST CONDITIONS:

1 g/l of surfactant tested 20 g/l of base detergent PARCO® 8801

RESULTS: cf. Table 3

TABLE 3

| VOLUME OF FOAM (ml) | 0 min | 1 min | 2 min | 3 min | 4 min | 5 min | 10 min | 15 min |
|---|---|---|---|---|---|---|---|---|
| *20° C.* | | | | | | | | |
| Good foaming agent IGEPAL 1064 | | 1170 | 1070 | 1010 | 960 | 940 | 850 | 700 |
| Poor foaming agent ANTAROX BL 330 | 120 | 80 | 60 | 50 | 50 | 50 | 30 | 20 |
| Non-foaming agent TETRONIC 701 | 0 | 0 | 0 | 0 | 0 | 0 | 0 | 0 |
| NOPOL 7.5 EO + 5.5 PO | 0 | 0 | 0 | 0 | 0 | 0 | 0 | 0 |
| NOPOL 2 PO + 5,1 EO | 5 | 5 | 5 | 5 | 5 | 5 | 0 | 0 |
| *50° C.* | | | | | | | | |
| Good foaming agent IGEPAL NP 1064 | 860 | 700 | 600 | 550 | 530 | 490 | 420 | 330 |
| Poor foaming agent IGEPAL NP 9 | 100 | 70 | 50 | 50 | 30 | 30 | 30 | |
| Very poor foaming agent ANTAROX BL 330 | 30 | 10 | 0 | 0 | 0 | 0 | 0 | 0 |
| Non-foaming agent TETRONIC 701 | 0 | 0 | 0 | 0 | 0 | 0 | 0 | 0 |
| NOPOL 7.5 EO + 5.5 PO | 0 | 0 | 0 | 0 | 0 | 0 | 0 | 0 |
| NOPOL 2 PO + 5.1 EO | 0 | 0 | 0 | 0 | 0 | 0 | 0 | 0 |

Under these test conditions, NOPOL 2 PO+5.1 EO and NOPOL 5.5 PO+7.5 EO are non-foaming surfactants at both 20° C. and 50° C. Their performance characteristics are similar to those of TETRONIC® 701 (PUCK), the compounds (Ia) being known to be better detergents than these TETRONICS®.

9.3 CLOUD POINTS:

| | |
|---|---|
| IGEPAL ® NP 1064 | 61° C. |
| ANTAROX ® BL 330 | 22° C. |
| TETRONIC ® 701 | 22° C. |
| NCPOL 7.5 EO + 5.5 PO | <20° C. |
| NCPOL 2 PO + 5.1 EO | 6° C. |

What is claimed is:

1. A surfactant composition which comprises at least one compound of the following formula (I):

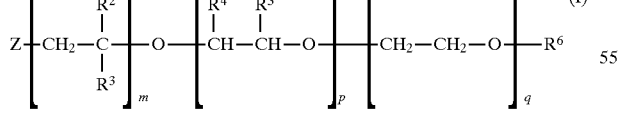

in which:

Z is a bicyclo[a.b.c]heptenyl or bicyclo[a.b.c]heptyl radical, wherein:
a+b+c=5,
a=2, 3 or 4,
b=2 or 1,
c=0 or 1,
said radical optionally being substituted by at least one $C_1$–$C_6$-alkyl, and comprising a skeleton of a formula selected from the group consisting of $Z_1$, $Z_2$, $Z_3$, $Z_4$, $Z_5$, $Z_6$, $Z_7$, and a respective heptyl analog thereof without the double bond:

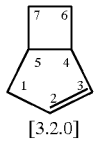

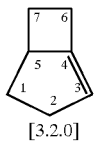

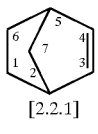

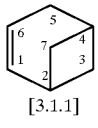

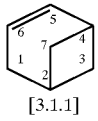

-continued

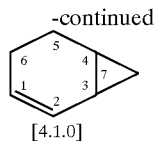
[4.1.0]
(Z₆)

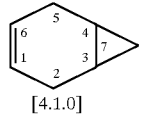
[4.1.0]
(Z₇)

wherein $R^2$ and $R^3$ are identical or different and are hydrogen or a linear or branched (cyclo)alkyl or (cyclo)alkenyl group;

and $R^4$ and $R^5$ are identical or different and are hydrogen or a linear or branched (cyclo)alkyl or (cyclo)alkenyl radical;

$R^6$ is hydrogen, $SO_3M$, $OPO_3(M)_2$, or $—(CH_2)_y—COOM$, wherein y is from 1 to 6, or $—(CH_2)_z—SO_3M$, wherein z is from 1 to 6; and M is H, Na, K, Li or $N(R^7)_4{}^+$, wherein $R^7$ is H or a $C_1$–$C_{22}$-(cyclo)alkyl, which is optionally hydroxylated;

m is 0 or 1;

$1 \leq p \leq 20$; and $1 \leq q \leq 200$;

with the proviso that when m is 0, at least one of $R^4$ and $R^5$ is other than hydrogen.

2. The surfactant composition according to claim 1, wherein the surfactant composition is non-foaming.

3. The surfactant composition according to claim 1, wherein the surfactant composition has a surfactant power which is adjustable according to the sum of p+q in formula (I).

4. The surfactant composition according to claim 1, wherein the Z radical is substituted on at least one of its carbons by at least two $C_1$–$C_6$-alkyl groups.

5. The surfactant composition according to claim 1, wherein m is 1 in formula (I).

6. The surfactant composition according to claim 5, wherein the Z radical comprises a skeleton selected from the group consisting of $Z_3$, $Z_4$, $Z_5$, $Z_6$, $Z_7$, and a respective heptyl analog thereof without the double bond.

7. The surfactant composition according to claim 6, wherein the Z radical comprising a skeleton is selected from the group consisting of $Z_4$, $Z_5$, and a respective heptyl analog thereof without the double bond.

8. The surfactant composition according to claim 1, wherein m is 0 in formula (I).

9. The surfactant composition according to claim 8, wherein the Z radical comprises the heptyl analog of skeleton $Z_3$ without the double bond.

10. The surfactant composition according to claim 9, wherein the Z radical comprises at least one alkyl radical substituent on carbon number 2 or 5 of the skeleton.

11. The surfactant composition according to claim 1, wherein the p and q repeating units of formula (I) are present in an amount and arranged so as to form a random or block polymer chain.

12. A fragrant composition which comprises at least one compound of the following formula (I):

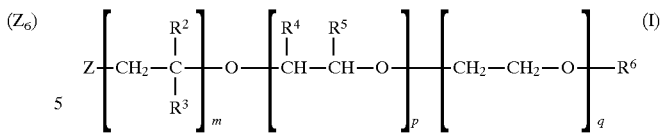

in which

Z is a bicyclo[a.b.c]heptenyl or bicyclo[a.b.c]heptyl radical, wherein:
a+b+c=5,
a=2, 3 or 4,
b=2 or 1,
c=0 or 1,
said radical optionally being substituted by at least one $C_1$–$C_6$-alkyl, and comprising a skeleton of a formula selected from the group consisting of $Z_1$, $Z_2$, $Z_3$, $Z_4$, $Z_5$, $Z_6$, $Z_7$, and a respective heptyl analog thereof without the double bond:

[3.2.0]
(Z₁)

[3.2.0]
(Z₂)

[2.2.1]
(Z₃)

[3.1.1]
(Z₄)

[3.1.1]
(Z₅)

[4.1.0]
(Z₆)

[4.1.0]
(Z₇)

wherein $R^2$ and $R^3$ are identical or different and are hydrogen or a linear or branched (cyclo)alkyl or (cyclo)alkenyl group;

$R^4$ and $R^5$ are identical or different and are hydrogen or a linear branched (cyclo)alkyl or (cyclo)alkenyl radical;

$R^6$ is hydrogen, $SO_3M$, $OPO_3(M)_2$, or $—(CH_2)_y—COOM$, wherein y is from 1 to 6, or $—(CH_2)_z—SO_3M$, wherein z is from 1 to 6; and M is H, Na, K, Li or $N(R^7)_4{}^+$, wherein $R^7$ is H or a $C_1$–$C_{22}$-(cyclo)alkyl, which is optionally hydroxylated;

m is 0 or 1;

$1 \leq p \leq 20$; and $1 \leq q \leq 200$;

with the proviso that when m is 0, at least one of $R^4$ and $R^5$ is other than hydrogen.

13. The fragrant composition according to claim 12, wherein the fragrant composition has a fragrant note which is adjustable according to the sum of p and q in formula (I).

14. The fragrant composition according to claim 12, wherein the Z radical is substituted on at least one of its carbons by at least two $C_1$–$C_6$-alkyl groups.

15. The fragrant composition according to claim 12, wherein m is 1 in formula (I).

16. The fragrant composition according to claim 15, wherein the Z radical comprises a skeleton selected from the group consisting of $Z_3$, $Z_4$, $Z_5$, $Z_6$, $Z_7$, and a respective heptyl analog thereof without the double bond.

17. The fragrant composition according to claim 16, wherein the Z radical comprising a skeleton is selected from the group consisting of $Z_4$, $Z_5$, and a respective heptyl analog thereof without the double bond.

18. The fragrant composition according to claim 12, wherein m is 0 in formula (I).

19. The fragrant composition according to claim 18, wherein the Z radical comprises the heptyl analog of skeleton $Z_3$, without the double bond.

20. The fragrant composition according to claim 19, wherein the Z radical comprises at least one alkyl radical substituent on carbon number 2 or 5 of the skeleton.

21. The fragrant composition according to claim 12, wherein the p and q repeating units of formula (I) are present in an amount and arranged so as to form a random or block polymer chain.

22. A surfactant and fragrant composition which comprises at least one compound of the following formula (I):

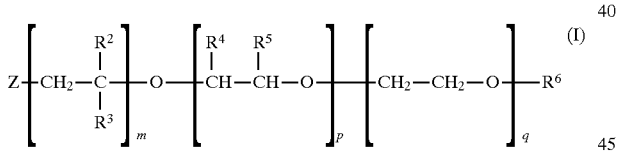

in which:

Z is a bicyclo[a.b.c]heptenyl or bicyclo[a.b.c]heptyl radical, wherein:

a+b+c=5, a=2, 3 or 4, b=2 or 1, c=0 or 1, said radical optionally being substituted by at least one $C_1$–$C_6$-alkyl, and comprising a skeleton of a formula selected from the group consisting of $Z_1$, $Z_2$, $Z_3$, $Z_4$, $Z_5$, $Z_6$, $Z_7$, and a respective heptyl analog thereof without the double bond:

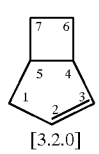
($Z_1$) [3.2.0]

-continued

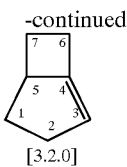
($Z_2$) [3.2.0]

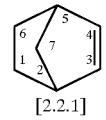
($Z_3$) [2.2.1]

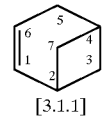
($Z_4$) [3.1.1]

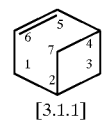
($Z_5$) [3.1.1]

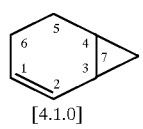
($Z_6$) [4.1.0]

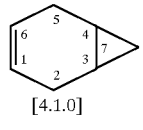
($Z_7$) [4.1.0]

wherein $R^2$ and $R^3$ are identical or different and are hydrogen or a linear or branched (cyclo)alkyl or (cyclo)alkenyl group;

$R^4$ and $R^5$ are identical or different and are hydrogen or a linear or branched (cyclo)alkyl or (cyclo)alkenyl radical;

$R^6$ is hydrogen, $SO_3M$, $OPO_3(M)_2$, or —$(CH_2)_y$—COOM, wherein y is from 1 to 6, or —$(CH_2)_z$—$SO_3M$, wherein z is from 1 to 6; and M is H, Na, K, Li or $N(R^7)_4^+$, wherein $R^7$ is H or a $C_1$–$C_{22}$-(cyclo)alkyl, which is optionally hydroxylated;

m is 0 or 1;

$1 \leq p \leq 20$; and $1 \leq q \leq 200$;

with the proviso that when m is 0, at least one of $R^4$ and $R^5$ is other than hydrogen.

23. A detergent formulation which contains one or more of a surfactant composition, a fragrant composition and a surfactant and fragrant composition, wherein the one or more of said compositions comprise at least one compound of the following formula (I):

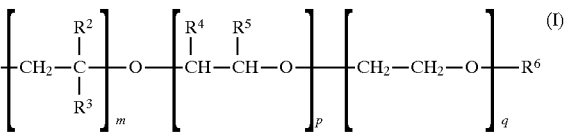

in which:

Z is a bicyclo[a.b.c]heptenyl or bicyclo[a.b.c]heptyl radical, wherein:

a+b+c=5, a=2, 3 or 4, b=2 or 1, c=0 or 1, said radical optionally being substituted by at least one C$_1$–C$_6$-alkyl, and comprising a skeleton of a formula selected from the group consisting of Z$_1$, Z$_2$, Z$_3$, Z$_4$, Z$_5$, Z$_6$, Z$_7$, and a respective heptyl analog thereof without the double bond:

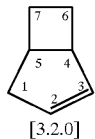
[3.2.0] (Z$_1$)

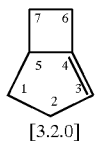
[3.2.0] (Z$_2$)

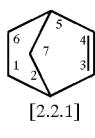
[2.2.1] (Z$_3$)

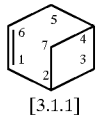
[3.1.1] (Z$_4$)

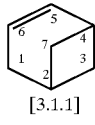
[3.1.1] (Z$_5$)

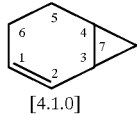
[4.1.0] (Z$_6$)

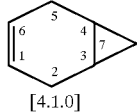
[4.1.0] (Z$_7$)

wherein R$^2$ and R$^3$ are identical or different and are hydrogen or a linear or branched (cyclo)alkyl or (cyclo)alkenyl group;

R$^4$ and R$^5$ are identical or different and are hydrogen or a linear or branched (cyclo)alkyl or (cyclo)alkenyl radical;

R$^6$ is hydrogen, SO$_3$M, OPO$_3$(M)$_2$, or —(CH$_2$)$_y$—COOM, wherein y is from 1 to 6, or —(CH$_2$)$_z$—SO$_3$M, wherein z is from 1 to 6; and M is H, Na, K, Li or N(R$^7$)$_4^+$, wherein R$^7$ is H or a C$_1$–C$_{22}$-(cyclo)alkyl, which is optionally hydroxylated;

m is 0 or 1;

1 ≤ p ≤ 20; and

1 ≤ q ≤ 200;

with the proviso that when m is 0, at least one of R$^4$ and R$^5$ is other than hydrogen.

* * * * *